United States Patent [19]
Klein

[11] 3,969,734
[45] July 13, 1976

[54] APPARATUS FOR RECORDING PNEUMATIC PRESSURES

[76] Inventor: Johann Klein, Overbeckstr. 2-4, 5 Cologne 30, Germany

[22] Filed: Aug. 8, 1974

[21] Appl. No.: 495,791

[30] Foreign Application Priority Data
Aug. 11, 1973 Germany.......................... 2340813

[52] U.S. Cl....................... 346/33 ME; 128/2.05 G; 128/2.05 M; 128/2.05 Q
[51] Int. Cl.²...................... G01D 5/06; A61B 5/02
[58] Field of Search.................. 128/2.05 Q, 2.05 G, 128/2.05 M, 2.05 A; 346/72, 32, 33 ME; 250/561

[56] References Cited
UNITED STATES PATENTS

| | | | |
|---|---|---|---|
| 3,623,478 | 11/1971 | Saba | 128/2.05 Q |
| 3,754,545 | 8/1973 | Weinstein | 128/2.05 Q |
| 3,771,515 | 11/1973 | Hurwitz | 128/2.05 G |
| 3,795,007 | 2/1974 | Mohrman et al. | 346/32 |
| 3,838,291 | 9/1974 | Marion et al. | 250/561 |

*Primary Examiner*—Kyle L. Howell
*Attorney, Agent, or Firm*—Steinberg & Blake

[57] ABSTRACT

An apparatus for recording pneumatic pressures such as those encountered when measuring blood pressure with a sphygmomanometer. A sheet material which is to have information recorded thereon is carried by a suitable support. A frame carries a marking instrument for marking the information on the sheet material, and in addition this frame carries a pressure-responsive device capable of responding to a change in pneumatic pressure and connected with the marking instrument for moving the latter in accordance with the degree of pneumatic pressure. A suitable structure is provided for moving the frame together with the marking instrument and the pneumatic pressure-responsive structure connected thereto from a non-marking position where the instrument is spaced from the sheet material to a marking position where the instrument engages the sheet material to record information thereon, and the structure which moves the frame to the marking position thereof brings about this operation in response to a change in the pressure which is received by the pressure-responsive structure.

7 Claims, 4 Drawing Figures

U.S. Patent    July 13, 1976    Sheet 2 of 2    3,969,734
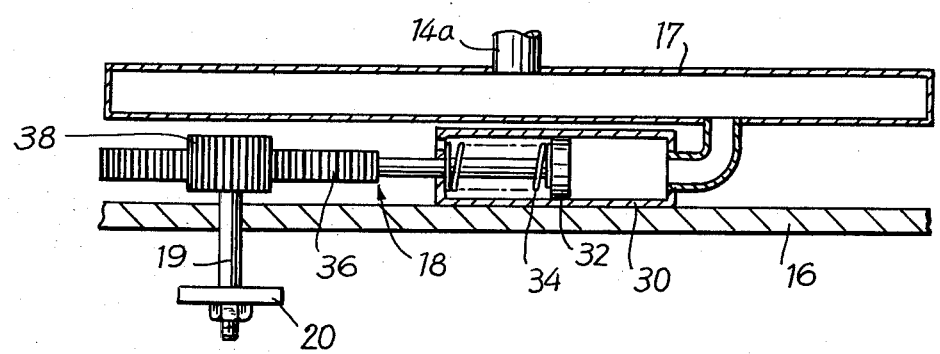
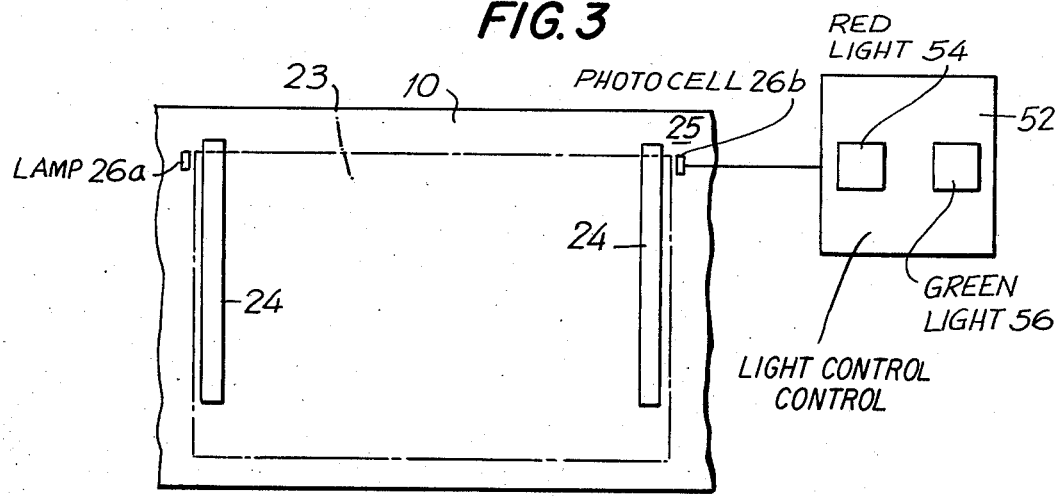
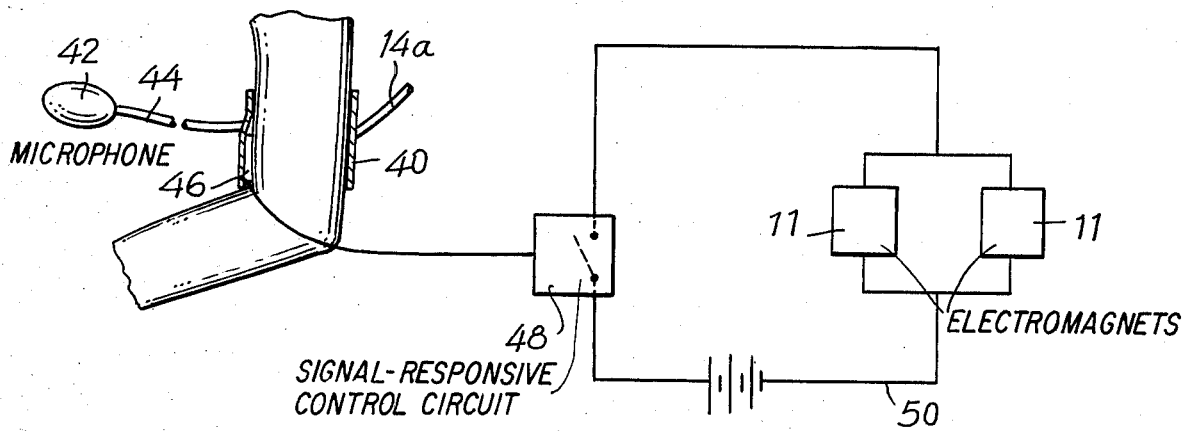

3,969,734

APPARATUS FOR RECORDING PNEUMATIC PRESSURES

BACKGROUND OF THE INVENTION

The present invention relates to devices for recording changes in pneumatic pressure, such as, for example, those encountered during measurement of blood pressure.

Thus, the present invention is particularly concerned with a device for recording values of pressure, in particular blood pressure, especially as derived from the use of a sphygmomanometer according to the Riva-Rocci/Korotkoff method.

With the invention a connection is made to the cuff of a sphygmomanometer in order to derive therefrom a pneumatic pressure which is then converted into a corresponding mechanical motion, the operation, being brought about in response to an electrical signal which initiates the operation of the recording device.

There are already known methods and devices for recording specific blood pressure values according to such methods, namely the systolic and/or diastolic pressure.

However, the known methods and devices require improvement. Thus, experience has shown that the known devices are of an extremely expensive construction so that, in spite of the importance of the information, when taking into consideration the purpose thereof, nevertheless the known constructions are too costly. The costs involved for both electronic and mechanical structures of the known devices is extremely high, inasmuch as it is not possible to provide known devices of this type without a special pressure transducer as well as an electronic amplifier, while on the other hand, the power supply components must be stabilized and several such components are required.

In connection with only the use of a recording device, it is required to have a complete drive for the paper strip which receives the recorded information, including a driving motor as well as transmission components, elements for guiding the paper strip, bearing components for the paper roll and the like. The large number of components required for this type of recorder results, however, in a relatively great loss of reliability in the operation.

Moreover, since, on the other hand, there are on the market a number of older blood pressure measuring devices including, for example, microphones, sphygmomanometer cuffs, and a simple device for introducing air under pressure into the cuff, there is also a need to complete such devices in a manner making it possible for them to be used for recording blood pressure, but up to the present time this requirement has not been satisfied.

Of considerable importance in this connection is also the fact that the sheet material used for recording information up to the present time is in the form of a paper recording strip providing only a limited accuracy in the reading of the values, such as is possible, for example, with a recording strip which has a width of 60 mm with graduations of 300 mm Hg pressure. At the same time, these units have the disadvantage of limiting a given body of information only to a part of the entire strip which also contains data in connection with other tests and individuals, so that additional administrative procedures are essential in order to select from a strip information which will be both accurate and complete. These latter procedures are relatively complex and in some cases result in errors.

SUMMARY OF THE INVENTION

It is accordingly a primary object of the present invention to provide apparatus which will avoid the above drawbacks.

In particular, it is an object of the present invention to provide a recording device of the above general type which is considerably simplified, particularly with respect to its electrical and mechanical structure, as compared with conventional recording devices, so that the costs can be lowered.

At the same time, it is an object of the present invention to provide a device of the above type which can be operated in an extremely simple manner while the possibility of faulty operation is greatly reduced.

Moreover, it is an object of the present invention to provide a recording apparatus which render it possible to record information in such a way that it is much simpler to examine the information and to administratively handle the information, as contrasted with conventional arrangements provided for the same purpose.

In accordance with the invention the recording device includes a support means for supporting a sheet material on which information is to be recorded. A frame means carries a marking means for marking information on the sheet material which is carried by the support means. A pneumatic pressure-responsive means is carried by the frame means and is operatively connected with the marking means for moving the latter in response to a change in the pressure of air which is received by the pneumatic pressure-responsive means. A moving means is operatively connected to the frame means for moving the latter from a non-marking position where the marking means is spaced from a sheet material carried by the support means to a marking position where the marking means engages a sheet material carried by the support means in response to a change in the pressure of air received by the pneumatic pressure-responsive means. Thus, in response to this change in air pressure the marking means will engage the sheet material to record the change in air pressure thereon.

BRIEF DESCRIPTION OF THE DRAWINGS

The invention is illustrated by way of example in the accompanying drawings which form part of this application and in which:

FIG. 2 is a transverse section schematically illustrating a pneumatic pressure-responsive means and the connection thereof to a marking means which is shown in FIG. 1;

FIG. 3 is a fragmentary top plan view of a support means for supporting sheet material on which information is to be recorded, the sheet material being shown in phantom lines in FIG. 3 with FIG. 3 also schematically illustrating a structure for signalling when the sheet material is properly positioned; and FIG. 4 is a schematic illustration of the apparatus of the invention for initiating a recording operation.

DESCRIPTION OF PREFERRED EMBODIMENTS

Figure 1:
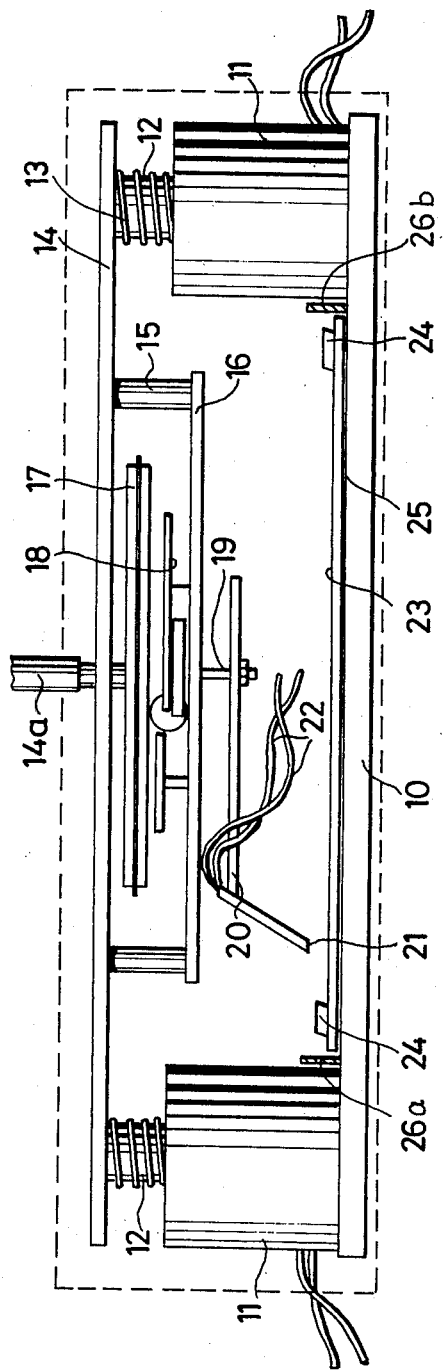
FIG. 1 is a schematic front elevation of a recording device according to the invention.

Referring to the drawings and to FIG. 1 in particular, it will be seen that the structure illustrated therein includes a base plate 10, or the like, carrying a moving means which is formed by a pair of electromagnets 11. The movable cores 12 of the electromagnets 11 extend through exciting coils 13 and are capable of being pulled downwardly, in response to energizing of the electromagnets, to a greater or lesser extent. The upper ends of the cores or armatures 12 of the electromagnets 11 are connected to, but insulated from, opposed end regions of an elongated plate 14 which forms part of a frame means which further includes the pins or rods 15 which are fixed to and extend downwardly from the plate 14, as well as a lower plate 16 which is fixed to the bottom ends of the pins or rods 15. Thus, the unit 14–16 forms a frame means capable of being moved toward or away from the support means 10 in response to energizing and deenergizing of the electromagnets 11. Suitable unillustrated springs maintain the frame means 14–16 in the non-marking elevated position illustrated in FIG. 1 when the electromagnets 11 are not energized.

The frame means 14–16 carries a pneumatic pressure-responsive means 17, 18 which is operatively connected with a marking means 21 for moving the latter in response to a change in the pressure of air received by the pressure-responsive means 17, 18. The portion 17 of the pressure-responsive means is in the form of a suitable enclosure which is capable of receiving air under pressure and which transmits the air under pressure to the means 18 (FIG. 2) which serves to convert a change in air pressure into a mechanical motion which provides for the marking means 21 a given turning moment so that the marking means 21 is turned.

As may be seen from FIG. 2, the interior of the enclosure 17 communicates with a cylinder 30 of the means 18, this cylinder 30 housing a piston 32 which is capable of being moved to the left, as viewed in FIG. 2, in opposition to the force of a spring 34, in response to an increase in air pressure. The left end wall of the cylinder 30 is formed with an opening communicating with the outer atmosphere and the spring 34 opposes the air pressure which engages the right face of the piston 32, as viewed in FIG. 2. Thus, as the pressure of the air in the enclosure 17 increases or decreases the piston 32 will move to the left or right, as viewed in FIG. 2. The piston rod which projects from the piston 32 to the left beyond the cylinder 30, as viewed in FIG. 2, is, in the illustrated example, fixed with an elongated rack 36 which forms an extension of the piston rod and which meshes with a pinion 38 fixed to the top end of a rotary shaft 19 supported for rotary movement in suitable bearings and extending through an opening of the plate 16. Beneath the plate 16 the rotary shaft 19 is fixed with a horizontally extending arm 20 which carries the marking means 21 which in the illustrated example is a known type of marking means capable of being heated by way of the electrical conductors 22 shown in FIG. 1.

Thus, the turning moment which is derived from the air pressure in the enclosure 17 is transmitted directly or indirectly by way of the shaft 19 to the arm 20 of the marking means 21.

Air under pressure is delivered to the interior of enclosure 17 by way of a flexible tube 14a, this tube 14a in turn communicating with the interior of a cuff 40 of a sphygmomanometer, as schematically illustrated in FIG. 4, this sphygmomanometer cuff 40 being capable of having the air pressure therein increased by repeated compression of a bulb 42 which communicates with the cuff through a tube 44 in a well known manner. As is well known, the pressure in the cuff 40 will be released when taking readings of systolic and diastolic pressure. Thus, by way of the transmission 18 the air pressure of the pressure-responsive means 17, 18 will turn the marking means 21 to angular positions which at any given instant correspond to the magnitude of the air pressure. The conductors 22 are connected to a suitable source of electrical energy for heating the electrically heatable marking instrument 21.

A sheet material 23 is situated beneath the marking means 21 to have information recorded on this sheet material 23 when it is engaged by the moving marking means 21. As is illustrated, the sheet material 23 preferably takes the form of a suitable file card whose positions on the support means 10 is determined by the gap between the upper surface 25 of the support means 10 and the lower surfaces of a pair of arms 24 which at their rear ends extend downwardly and are fixed to the support means 10, these arms 24 extending forwardly from their rear ends over the surface 25 while being spaced therefrom by a distance adequate to provide a gap slightly larger than the thickness of the sheet material 23. Thus the sheet material 23 can be slipped along the surface 25 beneath the arms 24 into engagement with the inner or rear ends thereof. This arrangement is also apparent from FIG. 3. The card 23 is provided with suitable scales which are printed thereon, these scales corresponding to normal blood pressure units in millimeters of mercury. In addition the card can have printed thereon suitable columns for such information as dates, names of individuals or identification of various test procedures, identification numbers, and the like.

As is shown schematically in FIG. 4, a microphone 46 is situated beneath the cuff 40 to respond to the Korotkoff sound, in a well known manner, transmitting in this way a signal to the schematically illustrated control unit 48 which serves by way of the schematically illustrated circuit 50 to energize the electromagnets 11 in response to the signal resulting from the Korotkoff sound. The termination of the Korotkoff sound and the signal derived therefrom serves to deenergize the electromagnets 11. Thus, through this simple control system shown in FIG. 4 it is possible to automatically excite the coils 13 to cause the moving means formed by the electromagnets 11 to pull the frame means 14–16 downwardly from the illustrated non-marking position to a marking position where the marking means 21 engages the sheet material 23 carried by the support means 10. It will be noted that the entire pressure-responsive means 17, 18 together with the marking means moves downwardly with the frame means. In this way the tip of the marking instrument 21 is placed in engagement with the sheet material 23. The heated tip of the instrument 21 thus records on the card 23, which has previously been placed in the position shown in FIGS. 1 and 3, a mark or trace which is indicative of the blood pressure. This mark or trace in the form of a suitable curve recorded on the sheet material 23 becomes situated adjacent a scale of pressure values previously printed on the card so that the blood pressure can be evaluated, and the recorded value is that which at the instant of recording prevails in the cuff 40, this pressure being the same as that which is in the enclosure 17, so that in this way the magnitude of the blood pressure is recorded. Upon termination of the Korotkoff sound the frame means is automatically returned to its non-marking position spacing the marking means 21 from the sheet 23.

As is apparent from the above, with the simple method and apparatus of the invention, utilizing only freely available relatively inexpensive components, and with practically no cost for electronic components, as well as very little possibility of faulty operation as a result of lack of a recording sheet material beneath the recording instrument, it is possible to achieve, nevertheless, an improved recording and accuracy in the manner in which the information is recorded and read. Moreover, it is possible, for example, to utilize with the sheet material formed by the card 23 scale graduations of 300 mm Hg on a scale length of 200 mm, as compared with the much smaller area and scale distribution provided with known recording strips.

The manner of reading the recorded information is the same as that utilized with normal pressure readings, with the same scale graduations and distribution being utilized. It is possible to use the entire card over its entire width for all types of data.

Of course, in individual cases it is possible within the scope of the invention to change one or another of the above-described details, for example in connection with the relationship of the components with respect to each other in connection with the type of measurement which is to be made, as well as in connection with the selection of the materials which are used and in connection with combining the structure of the invention with attachments, accessories, or the like.

Thus, the use of a marking means 21 which must be electrically heated is not essential. Instead it is possible to use a non-heated marking instrument which in this case can cooperate with a card 23 having a suitable coating on its surface which receives the tip of the marking instrument. This coating is made of a known material which is softer than the tip of the marking instrument and provides by color contrast with respect to the sheet material beneath the coating the required recording of the information. Thus the card itself may be made of a material which is brighter than the coating so that the coating serves to provide a color darker than that of the sheet material. The part of the coating which is removed by the harder tip of the marking instrument thus leaves a contrasting indication which serves to record the desired information on the card.

In order to avoid the operation of the structure when a card is not properly situated on the support means 10, as, for example, when the card is not moved in all the way up to the inner or rear ends of the arms 24, it is possible, in accordance with a further feature of the invention, to provide a sensing means which will indicate to the operator whether or not the card is properly positioned. Thus, in the illustrated example the sensing means is formed by the schematically illustrated components 26a and 26b. Components 26a may, for example, be a suitable lamp which through a suitable optical structure directs a beam of light beneath the arms 24 adjacent the inner rear ends thereof along the surface 25 of the support means 10 to a photocell 26b. Thus, only when the card 23 is properly positioned will the innermost or rear edge thereof interrupt the light beam. As is indicated schematically in FIG. 3 the photocell 26b is electrically connected with an indicating means 52 having, for example, a red light 54 which becomes illuminated when the light from the lamp 26a reaches the photocell 26b, *and having a green light 56 which becomes illuminated when the light travelling to the photocell 26b is interrupted by the card 23.* Thus, when the operator sees that the red light 54 is illuminated he will know that the card 23 has not been moved all the way into the compartment formed by the arms 24 together with the surface 25. However, when the card 23 is properly situated the light beam will be interrupted and the green light 56 will be illuminated indicating that the card is properly positioned.

It is to be noted that the particular structure described above and shown in FIGS. 1–3 is adapted to be used, in the manner shown schematically in FIG. 4, with the additional structure utilized for taking the blood pressure.

Moreover, the invention is not limited to methods and devices for recording blood pressure, but instead can also be used as required with other types of recording devices for indicating and maintaining measured values.

Thus, the invention can be used as a recording device or as an attachment or accessory for other recording purposes where pneumatic pressure values of any type are to be recorded. For example the method and apparatus of the invention may be used to provide control information for industrial or chemical processes, in order to measure monitor and/or regulate such processes. Also, even if the values to be recorded are not in the form of pneumatic pressures, it is possible nevertheless to utilize the invention by converting such values into corresponding pneumatic pressures.

Thus, in accordance with the invention the pneumatic pressure received by the enclosure 17 is converted into a turning moment which is transmitted to the turnable marking instrument capable of being moved toward and away from the sheet material on which the information is recorded. The structure for converting the pressure into a turning moment is made up of simple freely available components and the sheet material on which the information is recorded is also relatively simple, with the structure of the invention being capable of connection with a sphygmomanometer cuff, which is conventional, without any additional structures being required for this purpose. Inasmuch as the change in the air pressure is directly converted into a rotary movement of the marking means it is possible to achieve a considerable simplification and improvement of the recording and reading accuracy inasmuch as it is not essential to utilize with the recorder of the invention a relatively small recording strip.

Moreover, the quality of the recording is improved by utilizing for the marking means an instrument 21 which can be heated or not heated, this instrument having a relatively sharp tip which provides an accurate recording of the information. The enclosure 17 can take the form of a freely available conventional receptacle for receiving air under pressure and serves to reduce the cost of the structure. Moreover, it is possible to simplify the manner in which the recording of the information starts and ends by mounting the entire pressure-responsive means and marking means on a common movable frame means.

By utilizing one or more electromagnets 11 for the moving means, it is possible to provide a particularly quick and reliable recording in response to the Korotkoff sound, with the structure of the invention operating reliably to provide the upper systolic pressure value first in response to one impulse and then the lower diastolic pressure value in response to a second impulse, one directly after the other on the sheet material 23 in response to the Korotkoff signals.

Furthermore, the feature of the invention according to which a card such as a file card 23 is used for the sheet material to receive the recorded information is of particular advantage since it can easily be introduced into and removed from the apparatus and is made of a relatively stiff heavy paper or the like. The guide provided by the arms 24 and the surface 25 is particularly reliable for properly situating the sheet material 23. Moreover, a considerable advance is achieved with respect to conventional devices in that the card of the invention can be preliminarily printed so as to have the required information suitably recorded thereon, this information being, for example, the name, birth date, a file number or registration number, the date of the reading, and the like. Thus, by utilizing a file card instead of a recording strip, it is possible to take advantage of file cards which are already on hand and on which it is possible to record data in connection with blood pressure values, for example, both on the front face and the rear face of the card at different points in time, and these cards can be readily stored and taken from a suitable card filing system, thus enabling information to be recorded once or a number of times in the simplest possible manner.

Moreover, the positioning or guide structure formed by the arms 24 and the sensing means 26a, 26b assures that the desired printed area of the card is properly situated with respect to the marking means. Thus, the device of the invention is particularly suitable for utilizing a file card as the recording sheet material. Moreover, it will be seen that according to the invention the arrangement of the pneumatic pressure-responsive means with the pressure transducer which provides a turning moment enables the swingable marking means to be situated over the surface in such a way that a relatively shallow free space is maintained to receive the card in the space which is defined between the frame means 14–16, the electromagnets 11, and the base 10, so that in this way a relatively small free space of substantially rectangular configuration is readily available to receive the card in a simple effective manner.

Moreover, in accordance with the invention the recording device becomes automatically operative in response to starting or termination of the Korotkoff sound, as described above in connection with FIG. 4, so that in this way known controls can be used for initiating a recording operation, which is to say for energizing or deenergizing the electromagnets.

What is claimed is:

1. In a recording device, support means for supporting a sheet material on which information is to be recorded, frame means carrying a marking means for marking information on sheet material carried by said support means, pneumatic pressure-responsive means carried by said frame means and operatively connected with said marking means for moving the latter in response to a change in the pressure of air received by said pneumatic pressure-responsive means, moving means for responding to a predetermined signal and being operatively connected to said frame means for moving the latter in response to said signal from a non-marking position where said marking means is spaced from a sheet material carried by said support means to a marking position where said marking means engages a sheet material carried by said support means, said moving means maintaining said frame means and said pressure-responsive means and marking means carried thereby in said marking position while said signal is received by said moving means, and signal-transmitting means for transmitting said signal to said moving means in response to a given change in the pressure of air received by said pneumatic pressure-responsive means, said signal-transmitting means acting through said moving means for maintaining said frame means in said marking position while said signal is transmitted to said moving means, so that in response to said signal said marking means engages the sheet material to record thereon said change in air pressure which occurs during transmission of said signal to said moving means, said frame means including a plate which carries said pressure-responsive means and marking means, and said moving means including an electromagnetic means operatively connected with said plate for moving the latter toward said support means from said non-marking to said marking position.

2. The combination of claim 1 and wherein said marking means includes an electrically heatable marking element for engaging the sheet material.

3. The combination of claim 1 and wherein said pneumatic pressure-responsive means includes an enclosure for receiving air under pressure.

4. The combination of claim 3 and wherein said pneumatic pressure-responsive means includes in addition to said enclosure a motion-transmitting means for transmitting motion from said enclosure to said marking means for moving the latter according to the magnitude of the air pressure, said enclosure, said motion-transmitting means and said marking means all being carried by said frame means for movement therewith.

5. The combination of claim 1 and wherein said sheet material includes a card capable of being interchangeably placed on said support means to receive a mark from said marking means, and said support means carrying a positioning means for positioning said card with respect to said marking means.

6. The combination of claim 1 and wherein said pressure-responsive means receives air under pressure from a sphygmomanometer, and said signal-transmitting means including means responding to a Korotkoff sound for transmitting said signal and acting through said moving means for displacing said frame means between said positions thereof while maintaining said frame means in said marking position while the Korotkoff sound is received by said signal-transmitting means.

7. The combination of claim 1 and wherein the sheet material is in the form of a card carried by said support means, and electrical sensing means carried by said support means for sensing when said card has been positioned on the support means properly with respect to said marking means, and indicating means connected with said sensing means to be operated thereby for indicating whether or not the card has been properly positioned on said support means.

* * * * *